United States Patent
Klocke et al.

(10) Patent No.: US 8,709,073 B2
(45) Date of Patent: Apr. 29, 2014

(54) IMPLANT AND METHOD FOR PRODUCTION OF THE SAME

(75) Inventors: Bjoern Klocke, Zurich (CH); Ullrich Bayer, Admannshagen-Bargeshagen (DE)

(73) Assignee: BIOTRONIK VI Patent AG, Baar (CH)

( * ) Notice: Subject to any disclaimer, the term of this patent is extended or adjusted under 35 U.S.C. 154(b) by 197 days.

(21) Appl. No.: 12/820,639

(22) Filed: Jun. 22, 2010

(65) Prior Publication Data

US 2010/0324666 A1    Dec. 23, 2010

Related U.S. Application Data

(60) Provisional application No. 61/219,402, filed on Jun. 23, 2009.

(51) Int. Cl.
*A61F 2/06* (2013.01)

(52) U.S. Cl.
USPC ........................ 623/1.44; 427/2.25

(58) Field of Classification Search
None
See application file for complete search history.

(56) References Cited

U.S. PATENT DOCUMENTS

| | | | |
|---|---|---|---|
| 6,551,933 B1 * | 4/2003 | Molnar | 438/690 |
| 2004/0158330 A1 * | 8/2004 | M ller et al. | 623/23.57 |
| 2005/0079088 A1 * | 4/2005 | Wirth et al. | 420/402 |
| 2006/0229711 A1 * | 10/2006 | Yan et al. | 623/1.38 |
| 2008/0033538 A1 * | 2/2008 | Borck et al. | 623/1.46 |
| 2008/0082162 A1 * | 4/2008 | Boismier et al. | 623/1.38 |
| 2008/0243242 A1 * | 10/2008 | Kappelt et al. | 623/1.46 |
| 2009/0148496 A1 * | 6/2009 | Schmitz et al. | 424/426 |

OTHER PUBLICATIONS

Thierry et al ("Biocompatibility and Biostability of Metallic Endovascular Implants: State of the Art and Perspectives," J Endovasc ther 2003 10: 807-824) [Thierry].*

* cited by examiner

*Primary Examiner* — Suzanne Ziska
(74) *Attorney, Agent, or Firm* — Greer, Burns & Crain Ltd.

(57) ABSTRACT

One example embodiment of the present invention relates to an implant, particularly an intraluminal endoprosthesis, having a body that contains metallic material, preferably iron. The implant body has a first layer with at least one ionic compound that contains ions of at least one halogen, particularly chloride ions and/or bromide ions, on at least part of its surface. Furthermore, a method for the production of such an implant is described.

20 Claims, 3 Drawing Sheets

IMPLANT AND METHOD FOR PRODUCTION OF THE SAME

CROSS REFERENCE

This application claims priority on U.S. Provisional Application No. 61/219,402 filed on Jun. 23, 2009.

FIELD

Some embodiments of the present invention relate to an implant, with one example being an intraluminal endoprosthesis, having a body containing metallic material, preferably iron, particularly an iron alloy, as well as to methods for the production of such an implant.

BACKGROUND

Medical endoprostheses or implants for the most varied applications are known in great variety from the state of the art. Implants in this sense are understood to be endovascular prostheses or other endoprostheses, for example stents, attachment elements for bones, for example screws, plates, or nails, surgical suture material, attachment elements for artificial heart valves, intestinal clamps, prostheses in the sector of hard and soft tissue, as well as anchor elements for electrodes, particularly of pacemakers or defibrillators.

Nowadays, stents, which serve for the treatment of stenoses (blood vessel occlusions), are frequently used as implants. They have a body in the form of a tubular or hollow cylindrical basic lattice, at times with perforations, which is open at both longitudinal ends. The tubular basic lattice of such an endoprosthesis is inserted into the blood vessel to be treated, and serves to support the blood vessel. Stents have particularly established themselves for the treatment of vascular diseases. By means of the use of stents, it is possible to expand occluded regions in the blood vessels, so that a lumen gain is achieved. While it is true that an optimal blood vessel cross-section that is primarily required for therapy success can be achieved by means of the use of stents or other implants, the permanent presence of such a foreign body initiates a cascade of microbiological processes that can lead to the stent slowly becoming clogged due to accretion, and, in the worst case, to vascular occlusion. Aside from this phenomenon of restenosis, permanent implants have a number of other risks: chronic inflammation, lack of growing in, late thromboses, more difficult medical reintervention, uncontrolled fatigue ruptures, etc. One approach to solving these problems consists of making the stent or other implants from a biodegradable material.

Biodegradation is understood to mean chemical, hydrolytic, enzymatic and other metabolically related decomposition processes in the living organism, which are particularly caused by the bodily fluids that come into contact with the biodegradable material of the implant, and lead to gradual dissolution of the structures of the implant that contain the biodegradable material. As a result of this process, the implant may lose some or all of its mechanical integrity at a certain point in time. The term biocorrosion is often used as a synonym for the term biodegradation. The term bioresorption includes the subsequent resorption of the decomposition products by the living organism.

Implants with an iron alloy, particularly stents that contain iron, can be produced in particularly cost-advantageous and simple manner. However, for the treatment of stenoses, for example, these implants lose their mechanical integrity, i.e. support effect, only after a comparatively long period of time, i.e. only after having stayed in the treated organism for a period of approximately two years. This means that the dwell time of implants that contain iron is too long for some applications. For other applications of the iron-containing implants, for example in orthopedics, this applies analogously for iron-based implants and for implants made of other alloys, such as some magnesium alloys, for example (e.g. WE 43).

Different mechanisms of degradation control of implants may be based, for example, on inorganic and organic protective layers or combinations of them, which resist the human corrosion milieu and the corrosion processes that occur there. Barrier layer effects are achieved, which are based on a spatial and as defect-free as possible a separation of the corrosion medium from the metallic material. These lead to the result that the degradation time is extended. Thus, the degradation protection is assured by means of protective layers having different compositions, and by means of defined geometrical distances (diffusion barriers) between the corrosion medium and the degradable metallic basic body material. Other solutions are based on alloy components of the biodegradable material of the implant body, which influence the corrosion process by means of displacement of the position in the electrochemical voltage series. Other solutions in the field of controlled degradation bring about planned breakage effects by means of applying physical (e.g. local narrowing in cross-section) and/or chemical changes in the stent surface (e.g. multilayers having locally chemically different compositions). However, in the case of iron-based implants, it is generally not possible, using the solutions mentioned above, to place the dissolution that occurs as the result of the degradation process and the crosspiece breaks that result from this into the required time window, since the stated solutions essentially bring about a lengthening in the dwell time of the material. The result is either degradation of the implant that starts too late, or an overly great variability in degradation.

Another problem in connection with coatings results from the fact that stents or other implants usually assume two states, namely a compressed state with a small diameter, and an expanded state with a greater diameter. In the compressed state, the implant can be introduced into the blood vessel to be supported, and positioned at the location to be treated. At the treatment location, the implant is then dilated, for example by means of a balloon catheter, or (when using a shape memory alloy as the implant material) transformed into the expanded state by means of heating it above a jump temperature, for example. On the basis of this change in diameter, the body of the implant is subjected to mechanical stress when this occurs. Other mechanical stresses of the implant can occur during production, or during movement of the implant in or with the blood vessel into which the implant has been inserted. In the case of the aforementioned coatings, there is therefore the disadvantage that the coating might tear during deformation of the implant (e.g. due to the formation of micro-cracks) or is even partly removed. As a result, non-specific local degradation can occur. Furthermore, the onset and speed of degradation are dependent on the size and distribution of the micro-cracks that result from the deformation, and these are difficult to control, since the micro-cracks are defects. This leads to great variation in the degradation times.

SUMMARY

Consequently, one object of some embodiments of the present invention is creating an implant, which particularly has metallic material, and degrades during the desired target corridor, particularly in a shorter period of time. In this connection, the degradation is supposed to take place at a controllable point in time, and, in addition, the dilatation or deformation of the implant is supposed to have no noteworthy influence on the degradation behavior. Accordingly, other aspects of invention embodiments also consist of indicating a method for the production of such an implant, which method can be carried out in simple and cost-advantageous manner.

The above-stated objects as well as others are accomplished by means of an implant whose body has a first layer with an ionic compound (salt) on at least part of its surface, which compound contains ions of at least one halogen.

One example embodiment of the invention is an implant, particularly an intraluminal endoprosthesis, having a body containing metallic material characterized in that the implant body has a first layer on at least part of its surface, with at least one ionic compound that contains ions of at least one halogen.

Another example embodiment of the invention is a method for the production of an implant as described above, having a body that contains metallic material comprising the following steps:
  a) making available the body of the implant,
  b) applying the components of the first layer to at least a part of the surface of the implant body, where the ionic compound is applied separately from other components of the first layer.

Still another example embodiment of the invention is an intraluminal endoprosthesis implant comprising:
  a body comprising an iron alloy that contains at least 80% iron, the body having a surface;
  a first layer covering at least a portion of the body surface and comprising at least one ionic compound that contains at least one of chloride or bromide ions and further comprising at least one carrier from the group of polylactides, polyglycosides, copolymers of these polymers, and earth alkali phosphates, and;
  a second layer which covers at least part of the first layer and forms a diffusion barrier for the ions of the at least one halogen of the ionic compound, the second layer comprising one or more of magnesium stearate, parylene, and a pharmaceutically active substance.

DETAILED DESCRIPTION OF EXAMPLE EMBODIMENTS

Figure 1:
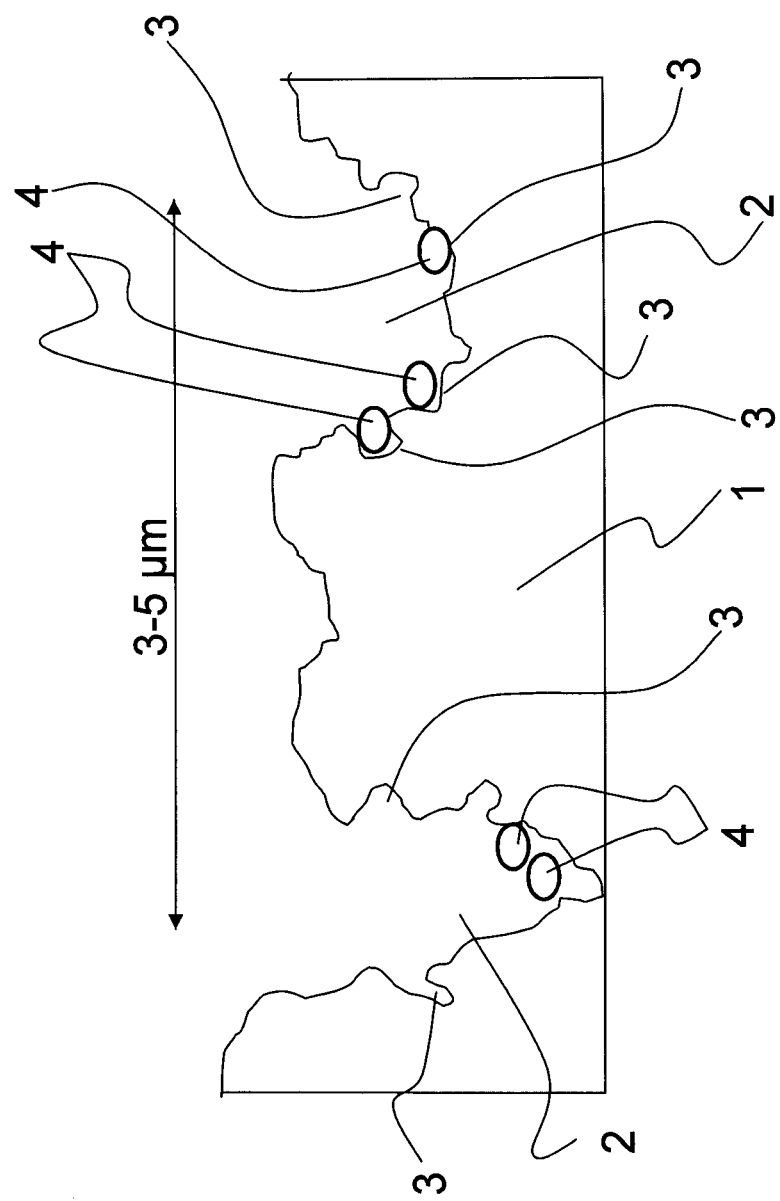
FIG. 1 a cross-section of a roughened surface of a first exemplary embodiment of an implant according to the invention, after 24 hours storage in a damp atmosphere (80% humidity) at 50° C., FIG. 2 a cross-section of an electrically supported tribochemical coating chamber, and FIG. 3 a cross-section of a second exemplary embodiment of an implant according to the invention.

This application claims priority on U.S. Provisional Application No. 61/219,402 filed on Jun. 23, 2009; which application is incorporated herein by reference.

Further aspects of example embodiments of the invention will be described herein below in greater detail. Before discussing such embodiments, comment on some suitable materials for use in some invention embodiments will be useful.

Materials that are suitable for the body of biodegradable implants of at least some invention embodiments can contain polymers or metals, for example. In this connection, the body can consist of several of these materials. The common characteristic of these materials is their biodegradability. Examples of suitable polymer compounds are polymers from the group of cellulose, collagen, albumin, casein, polysaccharide (PSAC), polylactide (PLA), poly-L-lactide (PLLA), polyglycol (PGA), poly-D,L-lactide-co-glycolide (PDLLAPGA), polyhydroxybutyric acid (PHB), polyhydroxyvaleric acid (PHV), polyalkylcarbonates, polyorthoesters, polyethylene terephthalate (PET), polymalonic acid (PML), polyanhydrides, polyphosphazenes, polyamino acids and their copolymers, as well as hyaluronic acid. Depending on the desired properties, the polymers can be present in pure form, in derivative form, in the form of blends, or as copolymers. Metallic biodegradable materials are predominantly based on alloys of magnesium and iron. Many embodiments of the present invention preferably relates to implants whose biodegradable material at least partly contains a metal, preferably iron, manganese, zinc and/or tungsten, particularly an iron-based alloy (hereinafter, for short: iron alloy).

In the implementation of biodegradable implants, one aim of some invention embodiments is to control the degradability in accordance with the therapy being aimed at, i.e. the use of the implant, in each instance (coronary, intracranial, renal, etc.). For many therapeutic applications, an important target corridor is, for example, that the implant loses its integrity over a time period of four weeks to six months, because after this time, the healing processes of the body have generally restored the mechanical function of the tissue. In this connection, integrity, i.e. mechanical integrity is understood to be the property that the implant possesses almost no mechanical losses as compared with the undegraded implant. This means that the implant is still so mechanically stable that the collapse pressure, for example, has dropped only slightly, i.e. at most to 80% of the nominal value. Thus, the implant can still fulfill its main function, that of holding the blood vessel up, when its integrity still exists. Alternatively, integrity can be defined in that the implant is so mechanically stable that it is subjected to hardly any geometric changes in the blood vessel in its stressed state, for example it does not collapse to any noteworthy degree, i.e. has at least 80% of the dilatation diameter under stress, or, in the case of a stent, has hardly any broken supporting crosspieces.

One example embodiment of the invention is an implant, particularly an intraluminal endoprosthesis, having a body containing metallic material characterized in that the implant body has a first layer on at least part of its surface, with at least one ionic compound that contains ions of at least one halogen.

The body of the some embodiments of an implant comprises at least a part of the implant, preferably the main part of the implant, which brings about the mechanical integrity of the implant. Furthermore, the first layer does not have to form a full-area coverage of the implant body, but rather can have regions in which the surface of the implant body is not or not completely covered.

The first layer disposed on the surface of the implant body, according to some embodiments of the invention, with the ionic compound, has the task of releasing halogenide ions, preferably chloride ions and/or bromide ions, in vivo. In this way, an increased concentration of these ions is achieved at the surface of the implant body, as compared with physiological conditions. This increased concentration of the halogenide ions, preferably of the chloride ions and/or bromide ions, has been discovered to promote the degradation of the material of the implant body that lies underneath. In this connection, concentrations of the chloride ions, for example, up to the saturation limit of NaCl in water can be implemented. The chloride and/or bromide ions or other halogenide ions that are present promote pitting corrosion and crack corrosion, with the latter taking place after the occurrence of the first cracks during dilatation or the occurrence of the first fatigue cracks as the result of pulsing stress on the implant in a blood vessel, for example. In these corrosion processes, the implant body is attached by way of different known mechanisms, particularly in spite of the presence of a passivation layer. The corrosion-reducing, natural oxide layer on the surface of a metallic material is referred to as a passivation layer.

In the case of what is called pitting corrosion, the oxygen of the passivation layer is displaced from the passivation layer of the implant body by the halogenide ions, for example the chloride and/or bromide ions. Due to the accumulation of additional chloride and/or bromide ions, a region is formed that is no longer protected by an oxide layer. This region forms an ideal point of attack for corrosion. In the case of crack corrosion, halogenide ions, for example the chloride and/or bromide ions, accumulate in the regions in which cracks are formed in the passivation layer as the result of dilatation or other mechanical stress, for example. In this way, corrosion is also promoted in the crack regions. Important advantages and benefits are accordingly achieved.

Another advantage of the first layer provided in some invention embodiments consists in that the adhesion of other functional layers that might lie on top of it, for example layers containing a pharmaceutically active substance or other materials, preferably polymer materials, is improved.

In an exemplary embodiment of the invention, intermediate layers that contain agents that promote adhesion or allow diffusion, or are degradable, can be provided in the first layer having the ionic compound.

In a particularly preferred exemplary embodiment, the ionic compound is a compound from the group that contains NaCl, $CaCl_2$ and $MgCl_2$. These compounds can be produced in particularly cost-advantageous manner, and are easy to handle.

In this connection, it is advantageous if the ionic compounds are stored under dry conditions, since in this way, the corrosion-accelerating effect of the salts can be controlled by means of providing a corresponding dissociating fluid, for example by installing the implant into an organism, and contact with a bodily fluid (blood, plasma).

In another preferred exemplary embodiment, the ionic compound can have at least one cation of the elements from the group that contains the elements of the first main group, the elements of the second main group, zinc and arsenic. These, together with the chloride and/or bromide ions, form ionic compounds that are easy to handle in production and are cost-advantageous. In a preferred exemplary embodiment, the ionic compound tied into the first layer can also have a positive effect on the surrounding tissue, by way of the cation, for example an anti-proliferative effect when using arsenic chloride as the ionic compound.

In another preferred exemplary embodiment, the first layer additionally has at least one carrier from the group that contains polylactide, polyglycosides, copolymers of these polymers and earth alkali phosphates and/or a second layer is provided, which at least partly covers the first layer, where the second layer (topcoat) forms a diffusion barrier for the ions of the at least one halogen of the ionic compound, particularly for the chloride and/or bromide ions.

The carrier and/or the second layer serve to hold the chloride and/or bromide ions essentially in the vicinity of the surface of the implant body (particularly during handling of the implant), so that they do not diffuse away into the surrounding tissue too quickly. Particularly by means of the application of a second layer, which preferably has polylactides, polyglycosides, copolymers of these polymers and earth alkali phosphates, the pH in the region of the surface of the implant body is reduced, i.e. its reduction is reinforced, or, depending on the material of the implant body, corrosion is made possible in the first place. In the case of use of a stent as the implant, complete decomposition of the stent body is generally achieved within a few months.

In another preferred exemplary embodiment, a third layer is provided at least on part of the first layer and, if applicable, the second layer, which third layer contains magnesium stearate and/or parylene and/or a pharmaceutically active substance. In the case of the presence of a carrier, the pharmaceutically active substance can also be embedded directly into the first (or second) layer.

A "pharmaceutically active substance" (or therapeutically active or effective substance) in the sense of the invention is understood to be an animal, vegetable, or synthetic active substance (medication) or a hormone, which finds use, in a suitable dose, as a therapeutic agent for influencing states or functions of the body, as a replacement for active substances naturally produced by the human or animal body, such as insulin, as well as for eliminating pathogens, tumors, cancer cells, or substances foreign to the body, or rendering them harmless. Release of the substance into the surroundings of the implant has a positive effect on the course of healing, or counteracts pathological changes of the tissue as the result of surgical intervention, or serves to render malignant cells harmless in oncology.

Many (but not all) of such pharmaceutically active substances have, for example, an anti-inflammatory and/or anti-proliferative and/or spasmolytic effect, which makes it possible to avoid restenoses, inflammations or (vascular) spasms, for example. Such substances can consist, for example, of one or more substances from the active substance group of calcium channel blockers, lipid regulators (such as fibrates, for example), immune suppressives, calcineurin inhibitors (such as tacrolimus, for example), anti-phlogistics (such as cortisone or dichlofenac, for example), anti-inflammatories (such as imidazole, for example), anti-allergies, oligonucleotides (such as dODN, for example), estrogens (such as genistein, for example), endothelium-forming agents (such as fibrin, for example), steroids, proteins, hormones, insulins, cytostatics, peptides, vasodilators (such as sartane, for example) and anti-proliferative substances, taxols or taxanes, here preferably paclitaxel or sirolimus, everolimus, biolimus A9, deforolimus and their derivatives or prodrugs.

Coating of the surface of the implant provided with the first layer and/or if applicable with the second layer, by means of parylene and/or magnesium stearate, is advantageous since the surface properties, for example the corrosion progress that is already reached during a post-treatment step, can be 'frozen' by means of the third layer that lies on top. In this way, the surface properties, which otherwise might depend on the storage or transport period of the implant until its introduction into the organism to be treated, and thus also the degradation period, can be adjusted in reproducible and defined manner. This effect is based on the action as a diffusion barrier with regard to the permeation of water molecules and halogenide ions, particularly chloride and bromide ions.

Parylene is the name for a special class of completely linear, partly crystalline, aromatic polymers. The different polymers possess different properties, and can be divided into four basic types, namely parylene C, parylene D, parylene N and parylene F. For further coating after the surface treatment with an ionic compound, parylene C is preferably used.

In the case of coating with parylene within some invention embodiments, it has been discovered that its great ability to penetrate cracks has an advantageous effect, so that even complicated geometries or non-planar surface structures can be coated. The permeation properties for water, solutions that contain chloride, and hydrogen that are characteristic for parylene, particularly parylene C, in combination with the underlying surface provided with an ionic compound, ensure that the degradation behavior of the implant will be particularly well controlled. Furthermore, the parylene layer makes an additional contribution to avoiding or hindering crack propagation under mechanical stress, and prevents partial loosening of layers.

In this connection, preferred layer thickness values of the parylene coating lie between about 0.5 µm and about 5.0 µm.

By means of the method according to the invention, in the case of the additional coating with magnesium stearate, an implant can be produced that is characterized by freedom from defects of the body surface, as the result of subsequent sealing. Local defects and/or pores present on the body surface of the implant and other non-planar surface structures are effectively protected from contact with bodily fluids that have a corrosive effect. The hydrophobic surface property and the low water of crystallization content of the magnesium stearate, which is also brought about by a drying step that is preferably carried out, subsequent to application of the magnesium stearate coating, bring about extremely low diffusion of water into the basic material of the implant body during subsequent storage and transport of the implant. Likewise, loosening of particles having a low tendency to bond to the surface of the implant body, during dilatation, is prevented. These particles remain in the viscous, highly flexible magnesium stearate layer. This results in increased hemocompatibility and biocompatibility. Accordingly, important advantages and benefits over the prior art are achieved.

Because of the magnesium stearate coating of the implant body, the result is achieved, in advantageous manner, that the friction coefficient of the implant decreases. From this, it follows that during displacement of a stent as an implant, in a catheter, for example, lower forces have to be applied. As a result, more precise stent fixation is made possible in the case of a stent. Furthermore, crimping and subsequent release of the implant at the location to be treated are simplified.

In a preferred exemplary embodiment of the method according to the invention, the magnesium stearate coating is applied by means of immersion in a solution, where the solution contains magnesium stearate and a solvent, preferably acetone and/or isopropanol, and preferably has a temperature between about 10° C. and the boiling point of the solvent, in each instance. Alternatively, the magnesium stearate layer can also be applied in such a manner that the aforementioned solution that contains magnesium stearate is sprayed onto the body of the implant (spray coating). In this connection, the part is suspended in a chamber, on a thin wire, and sprayed from all sides by means of a rotating plate (batch holder).

In a preferred exemplary embodiment, the effectiveness of the immersion process can be increased by means of applying a pressure that is less than the ambient pressure, preferably less than about 90% of the ambient pressure, i.e. the air pressure at the location where the immersion process is being carried out. The degasification effect that occurs in this connection leads to rapid filling of the filigree surface structure of the implant with magnesium stearate. After a dwell time of a few minutes in the solution, preferably at least about 2 minutes, the implant body, coated with magnesium stearate, is removed from the immersion bath and dried in a drying oven, at a temperature that is greater than room temperature, preferably greater than about 30° C. In this connection, it is particularly preferred if the drying temperature is as low as possible, i.e. lies between about 40° C. and about 70° C., since in this way, slow release/evaporation of the at least one solvent occurs, thereby producing a pore-free layer that contains magnesium stearate.

The preferred thickness of the magnesium stearate coating lies at about 0.5 µm to about 2.0 µm, preferably about 0.7 µm to about 1.0 µm. In this connection, the concentration of the magnesium stearate in the additional coating lies about between 80 wt. % and 100 wt. %. Other thicknesses and compositions are contemplated.

In a preferred exemplary embodiment, the body of the implant preferably contains a degradable metallic material, preferably predominantly iron, particularly more than 80 wt. % iron, particularly preferably at least 99 wt. % iron, particularly in an alloy. As other metallic materials, alternatively or in addition, manganese, zinc and/or tungsten can be used.

These implants are particularly used for the treatment of illnesses of the human or animal organism, because they can be produced in cost-advantageous manner. In the case of iron-containing implants, in particular, coating the surface with a first layer that contains an ionic compound with a halogenide ion leads to a reduced degradation period. In this way, a gap between the degradable and non-degradable alloys for implants is closed.

The above task is furthermore accomplished by means of a method comprising the following steps:
a) making available the body of the implant,
b) applying the components of the first layer with at least one ionic compound, which has ions of at least one halogen, preferably chloride ions and/or bromide ions, to at least part of the surface of the implant body (e.g. by means of wet chemistry immersion or spraying, and subsequent drying), where the ionic compound is preferably applied separately from other components of the first layer (e.g. by means of applying a polymer as a carrier in a mixture with a solvent, or by means of application using a plasma chemistry method).

Such a method is cost-advantageous and produces an implant that demonstrates the advantageous properties described above.

Application of the ionic compound to the surface of the implant body in the form of a coating is advantageous because in this way, degradation can also be controlled spatially, i.e. locally. In some cases, it is advantageous if first, fragmentation of the implant, i.e. targeted corrosion of the implant body in specific, pre-determined regions, is initiated, which then brings about significantly faster degradation than corrosion of the entire implant body at the same time. Fragmentation of the implant takes place in accelerated manner particularly in that the tissue is stressed with fewer metal ions, preferably iron ions, during fragmentation, per time unit, as compared with total corrosion, i.e. the metal ions, preferably iron ions, are released in smaller amounts. On the other hand, corrosion can advance more rapidly locally if non-degrading cathode regions are present in the implant. These promote corrosion. The geometry of the fragments can furthermore be pre-determined by means of a partial coating at locations that are supposed to degrade rapidly. As an example, fragments having dimensions below 200 µm are clearly less critical than large ones for use in an organism. This is particularly important if implants have not grown in due to a coating with a pharmaceutically active substance, up to the desired degradation time, and fragments of the implant project into the blood vessel that was treated, or can be washed away.

In the case of a stent, in particular, the coating can be applied in such a manner that the connectors of a stent degrade as quickly as possible, in order to achieve good bending flexibility. Furthermore, stent rings should only break once the supporting effect is no longer required, e.g. after 3 to 6 months. Furthermore, small fragments should only be formed once the stent has completely grown in (e.g. when the stent has been disposed at the treated location of the organism for approximately 4 weeks without a drug coating, or approximately 6 months with a drug coating).

In a preferred exemplary embodiment, before application of the first component of the first layer, an adhesion-promoting agent, preferably a silane or SiC, is applied. The silane leads to the formation of thin SiOx layers. Alternatively, however, a SiC coating can also be applied using PVD or PE-CVD methods.

Furthermore, sputtering methods can be used, with which thin (10-30 nm) $TiO_2$ or ZnO layers are applied to the endoprosthesis surfaces.

The adhesion-promoting agent improves the adhesion, i.e. bonding of the first layer to the body of the implant. In this connection, adhesion promotion is based both on chemical binding forces and on the shape fit that is brought about by means of micro-roughness of the coating.

It is furthermore preferred if the ionic compound of the first layer, with the halogenide ions, preferably the chloride ions and/or the bromide ions, is applied by means of immersion and/or spraying and/or atomization and/or by means of jet-blasting jet particles on during tribochemical treatment. The first layer with the at least one ionic compound can be cost-advantageously applied by means of the methods indicated.

For example, a porous carrier layer, for example calcium phosphate, can first be applied. Subsequently, the implant body provided with the calcium phosphate carrier layer is immersed in a brine having the at least one ionic compound, and afterwards dried.

If a polymer carrier is used, then it is advantageous with regard to production costs if it is assured, by means of a suitable selection of (biocompatible) cations and solvents, that a mixture of the polymer carrier and the ionic compound can be applied by means of an immersion or spraying method.

Preferably, when using a combination of polymer carrier and salt, the salt is applied separately from the polymer. For example, a partial polymer layer, i.e. a partial layer of the first layer, for example having a layer thickness between 1 µm to 5 µm, is applied first, by means of spraying. Afterwards, a microcrystalline salt is atomized on, for example 100 to 200 µg salt. This concludes application of the first layer. Subsequently, a second layer is applied, which has a polymer carrier having a layer thickness between 5 µm and 20 µm.

After coating of the implant produced in this manner, it is advantageous if the implant is packed in airtight manner for further storage, for example by means of using an inert gas or dessicant. In this way, the implant is stored under dry conditions, and the corrosion process does not proceed in uncontrolled manner during storage.

In the case of application of the ionic compound of the first layer by means of jet-blasting jet particles on during tribochemical treatment, the ionic compound is preferably applied as a reagent, in a sheath (micro-encapsulation), where the reagent encapsulated in the sheath forms the jet particle, in each instance. The micro-encapsulation is destroyed, for the most part, when it impacts the surface of the implant body, and the reagent is released. The reagent adheres to the surface of the implant body, if applicable with the material of the micro-encapsulation. This exemplary embodiment is based on the use of micro-encapsulated jet particles that are accelerated in the direction of the surface of the implant, where the acceleration in the direction of the implant surface takes place at different pressures, variable angles and distances.

Alternatively, the ionic compound can also be applied tribochemically without any micro-encapsulation. The salts applied adhere to the surface of the implant body.

For example, an exclusive use of corrosively active salts as jet particles is also possible. In particular, $MgCl_2$ stored under dry conditions is used as a grained salt having a defined grain size, without the addition of other hard substances that have an abrasive effect. $MgCl_2$ stored under dry conditions should be used because otherwise, there is the risk of clumping, due to the strong hygroscopy of the material.

Because of their low hardness, $MgCl_2$ particles do not bring about any significant mechanical surface changes, i.e. no significant surface roughening. However, a large proportion of the $MgCl_2$ particles adheres to the surface of the implant. During subsequent storage of the implant treated in this manner, under an extremely dry atmosphere and with the exclusion of air, corrosion of the surface is delayed at first. Only at the time of implantation and contact of the implant, for example a stent, with the bodily fluid, does the adhering $MgCl_2$ begin to have a strong corrosive effect, so that accelerated degradation takes place.

In the case of storage that is not exclusively dry, the $MgCl_2$ particles temporarily remain in the submicro-roughening that has been tribochemically produced, until they dissolve; they accelerate corrosion if moisture in the air is present, and thus increase the dimensions of the cavity of the submicro-roughening.

The salts that adhere to the surface of the implant body bring about accelerated corrosion of the surface, where the corrosion is also dependent on the subsequent treatment of the implant carried out after the tribochemical treatment. Preferably, jet particles that contain a hard substance material and bring about a mechanical change, preferably fissure formation, of the surface, are additionally used during the tribochemical treatment. Such hard substance materials are compounds from the group that contains oxides, particularly $Al_2O_3$, $SiO_2$, $ZrO_2$, carbides, particularly TiC, SiC, $B_4C$, $Be_2C$, oxycarbides, nitrides, particularly TiN, c-BN, $Si_3N_4$, AlN and TiAlN, natural or synthetic diamond, as well as boron.

All the jet particles applied tribochemically are situated at least partly on the surface of the implant body or at a slight depth in the implant body after completion of the tribochemical treatment.

In order to achieve effective destruction of the micro-encapsulation upon impact on the implant body surface, the micro-encapsulation preferably has at least one thermolabile and/or photolabile and/or mechanically labile planned breaking point. The thermolabile and/or photolabile wall of the micro-encapsulation is preferably formed by means of azo functions (—N═N—) or dioxy functions (—O—O—). Furthermore, mechanical planned breaking points can be provided in the micro-encapsulation on the basis of differences in wall thickness, which are implemented by means of a corresponding geometric surface structure of the micro-encapsulation. In this connection, the thinnest regions of the micro-encapsulation represent the mechanical planned breaking points, which break when the micro-encapsulated jet particles impact on the implant surface and bring about the desired release of the chemically active reagent disposed within the micro-encapsulation. In this connection, when the micro-encapsulated jet particles impact on the surface of the implant, first the micro-encapsulation, which consists of a polymer material, for example, is massively plastically deformed. The predominant part of the micro-encapsulation is destroyed when this occurs, the sheath bursts in the regions having the lowest wall thickness, and the chemical reagent disposed in the interior is exposed. The part of the micro-encapsulated jet particles that is not immediately bounced off or reflected from the implant surface, i.e. parts of the micro-encapsulation (sheath) and/or at least part of the reagent contained in the interior, adheres to the surface of the implant. In this way, a chemical reaction is set underway, in which the material of the implant, the material of the micro-encapsulation, and the exposed chemical reagent participate. Elevated humidity and an elevated temperature in the treatment chamber accelerate the corrosion process initiated by the chemical reaction.

Preferably, a biodegradable polymer is used as the material of the micro-encapsulation, and an active reagent that leads to degradation effects at the implant surface, which would not have come about in the same way if the individual components were acting alone, is used. For example, a reaction between a polymer such as PLA as the material of the micro-encapsulation and NaCl or $MgCl_2$ as the reagent brings about a strong shift in the pH at the surface of the implant, into the acidic range. The strong corrosion that sets in, particularly in a damp environment, leads to the formation of iron oxyhydroxides. These adhere only weakly to the material of the implant, and during the course of the continuing corrosion, the bodily fluid (plasma, blood) that contains chloride ions migrates underneath them. In this way, strong roughening of the surface of the implant is brought about, so that the surface content of the implant increases, and corrosion proceeds downward into the material. These effects already occur after only very short periods of time of a few seconds to minutes, and can be further reinforced by the corrosion of the implant material that is produced by means of the jet particles newly introduced during ongoing tribochemical surface treatment. In total, a roughened surface is therefore formed after the tribochemical surface treatment by means of micro-encapsulated jet particles, which surface is very well suited for further surface treatment (e.g. final immersion in biodegradable polymer) because of its roughness and surface activity.

In another preferred exemplary embodiment, the tribochemical treatment takes place in at least two steps, namely in a first step, tribochemical treatment by means of jet particles that exclusively or at least predominantly have an inert hard material takes place, and in a second step that follows the first step, tribochemical treatment by means of jet particles that have the at least one salt, at least in part, if necessary as a reagent in a micro-encapsulation, takes place.

In another preferred exemplary embodiment, after tribochemical treatment, storage of the tribochemically treated implant body at elevated humidity, particularly at a humidity greater than 80%, and/or at elevated temperature, particularly at a temperature of more than 50° C., takes place.

As a result of the subsequent treatment of the implant body as indicated, particularly after tribochemical treatment by means of bombardment with jet particles that contain the at least one salt, particularly accelerated corrosion of the body surface is achieved. This subsequent treatment, particularly the storage at elevated humidity, brings about the formation of very specific, locally qualitatively different pitting corrosion effects.

In the case of this exemplary embodiment of the method according to the invention, the implant is furthermore preferably removed from the chamber having the elevated humidity and/or elevated temperature (for example after 24 hours to 72 hours at a relative humidity of 80% to 98% at a temperature of about 20° C. to 90° C.) after a variable but predetermined action time, and intensively rinsed with distilled water, if necessary. In order to avoid further corrosion processes that then proceed in uncontrolled manner, the implant is subsequently provided with a usual corrosion inhibitor, for example magnesium stearate and/or parylene (see above), and stored under dry conditions. Alternatively, the treated implant can also be stored under inert gas. In the case of storage under inert gas, it is also possible to do without the corrosion inhibitor.

In another exemplary embodiment, the average particle size of the jet particles amounts to about 5 nm to about 20 µm, preferably about 1 µm to about 3 µm. This particle size has proven to be particularly advantageous in the case of typical geometries of implants, particularly stents (crosspiece widths approximately 100 µm). In the case of tribochemical treatment with particles having maximally a few µm, no plastic deformations of the implant structure occur. In the case of more robust orthopedic implants, jet particles having a particle size of up to 20 µm can be used. In this connection, the particle size is determined using a raster electron microscope (in the case of particle sizes less than or equal to 3 µm) or a light microscope (in the case of particle sizes greater than 3 µm). The electron-microscope or light-microscope images are measured, and the average particle size is determined from the measurement values, for example by forming the average (arithmetical average). Accordingly, the jet particles consist not of individual atoms, ions, or compounds, but rather of a group or a structure of atoms, ions, or molecular compounds. In general, the tribochemical treatment is carried out at room temperature, i.e. in the cold state of the implant body.

Tribochemical treatments can be performed with known jet-blasting systems, in simple and cost-advantageous manner. In order to guarantee tribochemical treatment of the entire surface of an implant having an opening or an enclosed cavity, preferably of a stent, in the method according to the invention, jet-blasting devices are used that use a mandrel as the jet nozzle. Such a mandrel has a diameter, in the region of its jet nozzles, that is clearly less than the diameter of the opening or of the cavity of the implant into which the mandrel is introduced for the treatment. For example, the mandrel of a jet-blasting device for jet-blasting the inside surface of a stent will have an outside diameter, in the region of its nozzles, that is clearly less than the inside diameter of the stent.

Alternatively, the tribochemical treatment can also take place in electrical alternating fields. This applies if electrically conductive particles (metals or hard substance particles such as TiN, for example) are used as jet particles. In this connection, the mandrel that functions as the jet nozzle and the perforated sleeve that surrounds the endoprosthesis and can serve as a particle reservoir, if necessary, are connected with an alternating voltage source. The implant serves as the counter-pole. In the tribochemical process that starts when the electrical contact is closed, the particles that lie at potential with regard to the endoprosthesis are accelerated out of the mandrel and the sleeve, in the direction toward the endoprosthesis.

Because of the adjustable potential difference, different acceleration effects occur, which in turn lead to different kinetic energies of the particles. In this way, the roughness of the body surface and the depth effect with regard to increasing the dislocation density are adjustable.

The above task is furthermore accomplished by means of an implant that can be obtained by means of one of the production methods described above. The surface morphologies and surface compositions that are formed by means of coating the implant body are characteristic for the treatment, and are recognizable on the finished implant.

Further aspects of some example methods and implants will be explained in further detail below, using the figures.

Although exemplary embodiments of the present invention are shown and described and have been discussed above, it should be apparent to those of ordinary skill that a number of changes, modifications to the invention and all possible combinations thereof and of the exemplary embodiments may be made without departing from the spirit and scope of the invention.

FIG. 1 shows a cross-section through the region close to the surface of a tribochemically treated implant 1. The surface has structures in the form of micro-roughening 2, which are formed by means of bombardment with large hard substance jet particles and/or jet particles having a higher kinetic energy. The depth of such micro-roughening amounts to several micrometers. The size ratios are shown by the arrow shown in the top of FIG. 1, which symbolizes a dimension of 3 μm to 5 μm. A high kinetic energy can be achieved both by means of a great mass of the jet particles, and by a great jet-blasting pressure, i.e. a high velocity of the jet particles. Furthermore, the kinetic energy can be varied by means of the electrical parameters of the alternating field, as explained above.

The submicro-roughening 3 contained in the surface profile (of the surface structure), which is clearly smaller than the micro-roughening 2, is formed by means of using small jet particles that contain salt, which adhere to the surface as salt particles 4 and immediately have a corrosive effect under humid ambient conditions. Furthermore, reactions that promote corrosion, initiated by means of jet-blasting micro-encapsulated jet particles on, which particles have planned breaking points in their micro-encapsulation, can be involved in the formation of submicro-roughening. The submicro-roughening 3 has a diameter, in each instance, of 0.1 μm to 0.5 μm.

Figure 2:
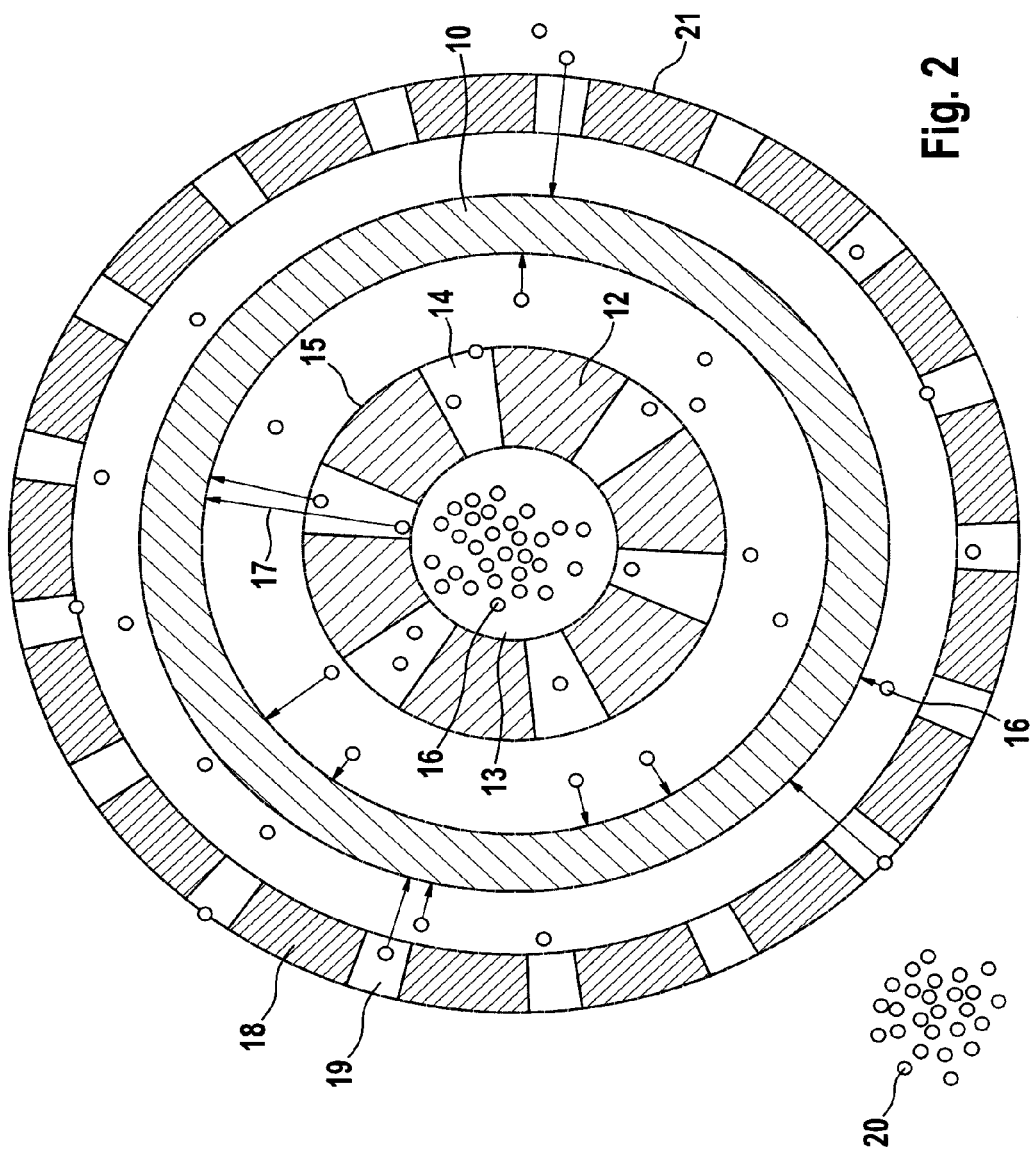

FIG. 2 shows a cross-section through a system by means of which the tribochemical jet-blasting can take place. For example, a stent 10 is tribochemically treated using the system; it has the form of a hollow cylinder and thus is shown as a circular ring in cross-section. A mandrel 12 having a center opening 13 provided at the mandrel tip, as well as passage openings 14 that run radially, is disposed in the inside volume of the stent 10. Furthermore, a sleeve 18 having passage openings 19 that run radially surrounds the stent 10. A reservoir of jet particles 16 is provided in the mandrel 12 and outside the sleeve 18, which particles are accelerated from the mandrel 12 to the stent 10, i.e. from the sleeve 18 to the surface of the stent 10. In this connection, the jet particles 16 move through the corresponding passage openings 14 and 19, respectively. The movement direction of the jet particles 16 is indicated by an arrow 17 for some of the jet particles. The particle reservoir of the sleeve 18 is shown merely schematically in FIG. 2, and provided with the reference symbol 20. An increase in the kinetic energy of the jet particles can take place by means of applying an electrical field. For this purpose, the stent 10, on the one hand, and the mandrel 12 or the sleeve 18, on the other hand, lie at a different electrical potential. In order to produce the potential difference, the mandrel 12 has a polarity 15, and the sleeve 18 has a polarity 21.

1$^{st}$ Example

Tribochemical Treatment of an Implant by Means of Hard Substance Jet Particles

A stent made from an iron-based alloy, having a body with the composition 99.5 wt. % Fe, other elements Mn, C, Si, P and S, is first produced according to the usual production methods (laser-cutting the tube (outside diameter 2.0 mm, wall thickness 125 μm), deburring using a file, electro-polishing for the purpose of rounding the edges, and removing the oxide surface). Alternatively, a C60 steel (steel with 0.60 wt. % carbon, rest iron) can be used. As another alternative, the use of an iron-based alloy with 12 wt. % to 20 wt. % Mn is possible. Other alternatives likewise can be used.

Subsequently, the tribochemical treatment takes place. For this purpose, the stent surface is tribochemically treated in a jet-blasting chamber, simultaneously on the inside and the outside, at a jet pressure of 5 bar, with TiC particles. In this connection, the average particle size is 2 μm. After a time of 3 to 5 minutes, this part of the process is terminated. The stent is removed from the treatment chamber and cleaned in ethanol, as an intermediate step. Afterwards, it is returned to the same jet-blasting chamber, in which a second method step now takes place. In this step, salt particles composed of $MgCl_2$ and sheathed with a polymer composed of polylactide (PLA) are jet-blasted onto the surface. These particles have an outside diameter of approximately 5 μm. The $MgCl_2$ particles that are in the interior have an irregular shape and have a maximal expanse of approximately 3 μm. When a jet-blasting pressure of also approximately 4 bar is applied, they burst when they impact the stent surface. The PLA fragments that form, and the $MgCl_2$ particles that are then exposed, adhere to the surface that was previously roughened using the TiC particles, for the most part. This means that the surface is covered with a layer having a thickness of up to 5 μm, at a treatment time of 5 to 10 min and as a function of the amount of particles jet-blasted onto the surface, which layer consists of fragments of the polymer sheath and the exposed $MgCl_2$.

Optionally, there is the possibility of further improving adhesion in that the stent is treated with a sol-gel method (immersion method) before the tribochemical treatment, and subsequently tempered. In this way, a layer of adhesion-promoting agent, composed of $SiO_x$, and having a thickness of up to 20 nm, is produced. This $SiO_x$ layer brings about greater adhesion of the jet particles, i.e. their fragments to the stent surface. As an alternative to a $SiO_x$ layer, a SiC layer can also be applied as an adhesion-promoting agent, by means of PVD or PE-CVD.

The surface of the stent obtained in this way demonstrates an increased corrosion tendency both at high humidity and in vivo. The PLA hydrolyzes and is metabolized in vivo, during the further course of events. The $MgCl_2$ accelerates the iron corrosion. Greater formation of iron hydroxide and iron oxy-hydroxide occurs at the stent surface. This rust, as expected, demonstrates only a loose connection with the basic material here, too. Loose corrosion products are torn off, so that metallic surfaces are exposed, again and again. In comparison with an untreated iron-based stent having the identical composition, the corrosion-related mass loss in vivo is between 50% and 100% higher during the same period.

The first example relates to tribochemical treatment of an implant by means of hard particles. The hard particles consist of a mixture of micro-scale jet particles of TiC, WC and TiCN. The average grain size of the jet particles is 4 μm, with a variation of +/−1 μm. The tribochemical treatment takes place in a tribochemical system. The jet particles are jet-blasted simultaneously onto the inside and outside of the implant, by means of compressed air at 3 to 4 bar pressure, using the jet-blasting system shown in FIG. 2. The process takes place over a time period of 5 minutes. As a result, elastic and plastic deformation effects occur at the surface of the implant. The plastic deformation component leaves the surface morphology shown in FIG. 1 (without the submicro-roughening that forms by means of the subsequent salts).

Micro-hardness studies of an implant made of pure iron and treated in this manner have shown that a micro-hardness increased by up to 150 HV 0.1 is present at a roughened depth of 10 μm, in comparison with the component interior, in the volume region close to the surface that was plastically deformed by the jet particles.

$2^{nd}$ Example

Tribochemical Treatment of an Implant by Means of Jet Particles Composed of Salts The salts consist of a mixture of 50 mass-% NaCl and $MgCl_2$ each. The particle size of the salts used can vary within a broad range (2 μm to 200 μm) in the case of this exemplary embodiment, since the salt particles fragment to smaller fragments when they impact the stent surface. They are jet-blasted onto the surface that has already been damaged by means of the hard substance particles described in exemplary embodiment 1. The process is carried out in a tribochemical treatment system shown in FIG. 2, in section, at the pressures indicated in example 1. In order to avoid clumping of the hygroscopic salt mixture, it must be stored under dry conditions before and during the tribochemical treatment process.

In addition to or as an alternative to applying compressed air, the sleeve and the mandrel can have a different electrical potential, as compared with the implant, applied to them. This leads to electrical charging of the salt particles. From this, increased acceleration of the particles in the direction of the implant surface results, as compared with the current-free treatment variant. An increased temporary adhesion of the salts in the micro-roughening, and the resulting stronger formation of submicro-roughening, are the result.

$3^{rd}$ Example

Like One of Examples 1 to 2 and Additional Further Coating by Means of Parylene, Magnesium Stearate and/or Pharmaceutically Active Substance On the basis of the exemplary embodiments indicated above, as a final treatment step, coating with the materials indicated above can take place. Coating with parylene C takes place from the gas phase. After approximately a half hour of coating time, a layer thickness of approximately 0.5 μm is achieved.

In this connection, the parylene coating pursues the goal of temporary corrosion protection. The "pre-damaged" surface state is "frozen". Thus, no uncontrolled independently occurring degradation takes place before placement of the endoprosthesis at the place of use.

The same goal is pursued with the magnesium stearate coating described below. After the exemplary embodiments 1 and 2 are carried out, and after subsequent drying, the endoprosthesis is suspended on a synthetic thread (e.g. polyamide) and subsequently immersed in the solution for applying the magnesium stearate. The solution consists, for example, of 9 parts highly pure acetone or isopropanol, and 1 part magnesium stearate. The immersion process takes place at room temperature, in an exsiccator that can be evacuated. In this exsiccator, a partial vacuum of approximately 100 mbar is produced by means of a pump. In this way, the filigree micro-porous surface structures that were formed by the preceding plasma chemistry pretreatment, i.e. the undercuts and structures having a complicated shape, are effectively freed of residual gas. As a result, complete coverage of the stent surface by the magnesium stearate can take place in the solution, penetrating even into the surface structures and undercuts. After a dwell time of about 3 minutes in the immersion bath, the exsiccator is ventilated, the implant is removed from the immersion bath and subsequently dried in a circulating air cabinet, still hanging from the synthetic thread, at a temperature of 60° C. The layer thickness of the magnesium stearate coating obtained in this manner lies in the range of 0.5 to 10 μm.

Because of the partial vacuum that is present in the exsiccator, the magnesium stearate is deposited very uniformly on the surface. A low drying temperature advantageously brings about a slow release/evaporation of the solvent of the immersion solution, so that a pore-free magnesium stearate layer is formed. If the implant treated in this manner is a stent, then the body provided with the first layer and the intermediate layer can subsequently be completed with a catheter, and subjected to irradiation sterilization.

Analogous to the production of the parylene or magnesium stearate coating, the surface of the implant can alternatively or additionally be coated with a pharmaceutically active substance. Preferred substances are indicated above, in the specification.

$4^{th}$ Example

Figure 3:
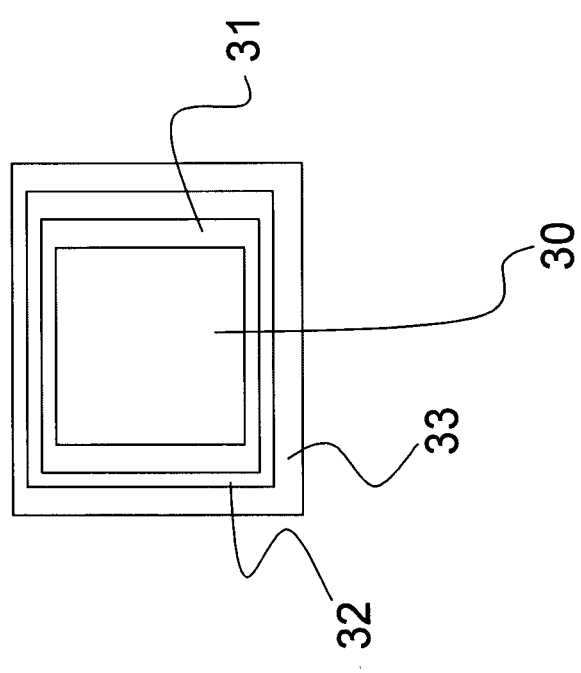

Tribochemical Treatment with Hard Substance Particles and Subsequent Application of an Adhesion-Promoting Layer for the Salts, and Subsequent Parylene or Magnesium Stearate Coating FIG. 3 shows a cross-section of a stent crosspiece that has a body 30 consisting of an iron-based alloy. Production of this stent took place as follows:

On the surface of the body 30, which has a cross-section of approximately 100 μm×100 μm, there is a first layer 31 that has adhesion-promoting properties. This layer consists of layers of $SiO_x$ or SiC or $TiO_2$ or ZnO having a thickness of 10 to 30 nm. This adhesion-promoting layer is applied to the surface of the body 30 that was previously tribochemically treated with hard substance particles. This surface treatment with inert hard substances only leads to surface consolidation and a related increase in defect density in the edge regions close to the surface. Since no material fit with these particles occurs, this is also not a component of the cross-section. The layer 31 that consists of $TiO_2$, for example, is produced using a known sputtering method or high-rate atomization. Both methods are carried out under vacuum conditions. An oxygen partial pressure that must be implemented in the treatment chamber during the process, and the titanium that is present in the coating chamber as the target material, lead to the formation of thin $TiO_2$ layers on the stent surface, under the conditions of physical vapor deposition (PVD).

This also applies analogously for the other oxide adhesion-promoting layers. On the first layer 31, there lies a second layer 32 composed of adhered salts composed of 50 mass-% $MgCl_2$ and 50 mass-% NaCl, which has a layer thickness of maximally 5 μm. On this, there is a third layer 33 composed of up to 10 μm magnesium stearate. Its production was carried out as described in exemplary embodiment 3. The layers 31, 32 and 33 have a total layer thickness in the range of 1 μm to 15 μm.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

REFERENCE SYMBOL LIST 1 implant body
2 micro-roughening
3 submicro-roughening
4 adhered salt particle
10 stent
12 mandrel
13 opening
14 passage opening for jet particles 16
15 polarity of the mandrel
16 jet particle
17 arrow (movement direction of the jet particle 16, in each instance)
18 sleeve
19 passage opening for jet particles 16
20 jet particle reservoir of the sleeve 18
21 polarity of the sleeve 18
30 implant body
31 first layer
32 second layer
33 third layer

What is claimed:

1. An implant comprising:
   a body containing metallic material;
   a first degradation promoting layer on at least part of a surface of the body, with at least one ionic compound that contains ions of at least one halogen, the ions promoting the degradation of the body below the degradation promoting layer; and
   a magnesium stearate containing layer disposed at least on a part of the first degradation promoting layer.

2. The implant according to claim 1, characterized in that the ionic compound contains at least one of chloride ions and bromide ions that promote one or more of pitting and crack corrosion of the body.

3. The implant according to claim 1, characterized in that the ionic compound is a compound from the group that contains NaCl, $CaCl_2$ and $MgCl_2$.

4. The implant according to claim 1, characterized in that the first degradation promoting layer includes at least one carrier from the group that contains polylactides, polyglycosides, copolymers of these polymers, and earth alkali phosphates.

5. The implant according to claim 1 wherein a second layer is provided, which covers the first degradation promoting layer at least in part and forms a diffusion barrier for the ions of the at least one halogen of the ionic compound and that is operative to prevent diffusion of the ions and to thereby hold the ions in place in the vicinity of the body, and wherein the magnesium stearate layer is disposed on at least a part of the second layer.

6. The implant according to claim 1, characterized in that the ionic compound has at least one cation of the elements from the group of elements of a first main group of the periodic table, elements of a second main group of the periodic table, zinc and arsenic.

7. The implant according to claim 1, characterized in that the magnesium stearate containing layer further contains parylene, a pharmaceutically active substance, or both.

8. The implant according to claim 1, characterized in that the body of the implant predominantly contains iron, wherein a corrosion reducing passivation layer containing oxygen is formed on the surface of the body, and wherein the halogen ions displace the oxygen from the passivation layer to promote pitting of the body surface.

9. The implant according to claim 8 wherein the iron is provided in an alloy that contains more than 80 wt % iron, wherein the body has at least a crack, wherein a passivation layer forms over at least portions of the body, and wherein the halogenide ions from the degradation promoting layer accumulate in regions where cracks are formed in the passivation layer as the result of dilation or other mechanical stress to promote corrosion in the regions where the cracks are formed.

10. The implant according to claim 8 wherein the body contains more than 99 wt. % iron in an alloy.

11. A method for the production of an implant comprising the following steps:
   a) coating at least a portion of the implant body with a first layer comprising at least one ionic compound that contains ions of at least one halogen; and
   b) coating a magnesium stearate-containing layer on at least a part of the first layer.

12. The method according to claim 11, characterized in that the adhesion-promoting agent is applied at least in regions on which the first layer is subsequently disposed.

13. The method according to claim 11, characterized in that at least the ionic compound of the first layer is applied by one or more of steps of immersion, spraying, atomization and jet-blasting jet particles on during a tribochemical treatment.

14. The method according to claim 13, characterized in that the tribochemical treatment takes place in at least two steps, namely in a first step, tribochemical treatment by means of jet particles that contain an inert hard material, and in a second step that follows the first, tribochemical treatment by means of jet particles that contain the ionic compound.

15. The method according to claim 13, characterized in that after tribochemical treatment, the tribochemically treated implant body is stored at a humidity greater than 80% and a temperature of more than 50° C.

16. The method according to claim 13, characterized in that the jet particles contain the ionic compound are in a microencapsulation.

17. The method according to claim 16 wherein the microencapsulation has at least one of a thermolabile, photolabile planned breaking point and a mechanically labile planned breaking point.

18. The method of claim 11 wherein the implant is intraluminal endoprosthesis, and includes a body that contains iron.

19. The method according to claim 11 wherein the ions from the first layer promote degradation of the underlying body through one or more of pitting or cracking.

20. An intraluminal endoprosthesis implant comprising:
   a body comprising an iron alloy that contains at least 80% iron, the body having a surface;
   a corrosion promoting layer covering at least a portion of the body surface and comprising at least one ionic compound that contains at least one of chloride or bromide ions and further comprising earth alkali phosphates, the at least one chloride or bromide ions promoting corrosion of the body under the corrosion promoting layer;
   an adhesion promoting agent between the body surface and the corrosion promoting layer;
   a barrier layer which covers at least part of the first layer and forms a diffusion barrier that holds the at least one chloride or bromide ions in the vicinity of the body to enhance the corrosive effect of the ions; and
   a magnesium stearate containing layer disposed on at least a part of the barrier layer, the corrosion promoting layer, or both, the magnesium stearate containing layer optionally including one or more of parylene or a pharmaceutically active substance.

* * * * *